United States Patent [19]

Chiou et al.

[11] Patent Number: 4,865,599

[45] Date of Patent: Sep. 12, 1989

[54] OPHTHALMIC COMPOSITIONS FOR TREATING NERVE DEGENERATION

[75] Inventors: George C. Y. Chiou, College Station; Dominic M. Lam, The Woodlands, both of Tex.

[73] Assignee: Houston Biotechnology, Inc., Woodlands, Tex.

[21] Appl. No.: 91,883

[22] Filed: Sep. 1, 1987

Related U.S. Application Data

[63] Continuation-in-part of Ser. No. 897,744, Aug. 18, 1986, abandoned.

[51] Int. Cl.$^4$ .............................................. A01N 25/26
[52] U.S. Cl. ...................................................... 424/427
[58] Field of Search ............................... 424/427–429; 604/890, 892, 894, 896, 897, 294; 514/912–913

[56] References Cited

U.S. PATENT DOCUMENTS

| | | | |
|---|---|---|---|
| 4,186,184 | 9/1987 | Zaffaroni | 604/893 |
| 4,591,600 | 5/1986 | Creuzet et al. | 514/465 |
| 4,721,713 | 1/1988 | Hayashi et al. | 514/255 |

OTHER PUBLICATIONS

Chemical Abstracts vol. 99: 43466t, *Study on the Prevention of Tetramethylpyrazine Eye Drop for the Prevention and Therapy of Nearsightedness in Youngsters,* Hu et al., Zhonhcaoyao 1983, 14(5), 208–10.
Pharmacology and Applications of Chinese Material Medica (Vol. 1) Eds. Chang and But, Translated by Yao and Wang, 1986.
Shi et al., (1979) 2:98 Medical Journal of Chinese Pla.
Shi et al., (1980) 60:623, National Medical Journal of China.
Shih, The Rheological Effect of Ligusticum Wallichii Franch, Medical Journal of the People'Liberation Army (1979) 4:98–103.

*Primary Examiner*—Stephen C. Pellegrino
*Assistant Examiner*—Sharon Rose

[57] ABSTRACT

Methods are provided for improvement in retinal and choroidal blood flow. The compounds can be administered topically or systemically to enhance the retinal blood flow in a variety of physiologically acceptable formulations.

5 Claims, 1 Drawing Sheet

OPHTHALMIC COMPOSITIONS FOR TREATING NERVE DEGENERATION

CROSS-REFERENCE TO RELATED APPLICATIONS

This application is a continuation-in-part of application Ser. No. 897,744, filed Aug. 18, 1986, now abandoned.

TECHNICAL FIELD

Tetraalkylpyrazine compounds are employed for enhancing retinal blood flow and preventing more degeneration.

BACKGROUND

The retina is supplied with oxygen and nutrients by two vascular systems, one within the retina itself (central retinal artery) and one in the choroid (posterior ciliary artery). Interruption or impairment of either system leads to degeneration of the retina and ultimately to loss of vision. There are many causes that effect retinal circulation and nutrient supply. Included among diseases and conditions are retinitis pigmentosa, diabetic retinopathy, sickle cell retinopathy, hypertensive and atheroscelerotic vascular diseases, retinal vein occlusion, maculopathy, and glaucoma (LaVaio et al., (1985); U.S. Department of Health and Human Services, (1983)). By providing for enhanced blood flow or nutrient supply to the retina, particularly early in the course of the above indicated diseases, prevention or slowing of vision loss may be achieved. Any drug, given systemically or locally to the eye, that is directed toward a disease symptom but results in a decrease in ocular circulation as a side effect, will normally enhance the visual deterioration, rather than improve it.

Glaucoma serves as an illustration of the problem, where glaucoma is treated by decreasing intraocular pressure (IOP) in order to improve optic nerve, choroidal and retinal circulation. It is found that some patients show retinal degeneration with normal IOP (low tension glaucoma), while others have abnormally increased IOPs with no visual disturbances. This may suggest that the correlation between IOP and retinal circulation is tenuous. A drug may lower IOP and concomitantly decrease retinal and choroidal blood flow (RCBF), leading to the false conclusion that the glaucoma is under control, while in fact retinal damage continues. It is therefore of substantial interest o find drugs which increase ocular circulation as their mechanism with the resulting IOP decrease.

RELEVANT LITERATURE

Ojewole, *Planta Medica* (1981) 43: 1–10 describes the blockade of adrenergic and cholinergic transmissions by tetramethylpyrazine. Ojewole, *Planta Medica* (1981) 42: 223–228 describes the effects of tetramethylpyrazine on isolated atria of the guinea pig. Gio et al., *Planta Medica* (1983) 47: 89 report the use of tetramethylpyrazine in the treatment of cardiovascular and cerebrovascular diseases. Dai and Bache, *J. of Cardiovascular Pharmacology* (1985) 7: 841–849 report the coronary and septemic hemodynamic effects of tetramethylpyrazine in a dog. Ohta et al. describe the preparation of tetraalkyl-substituted pyrazines.

Tetramethylpyrazine is one of the active principles isolated from *L. wallichii* (Chen, 1981; Chengdu College of Traditional Medicine, 1950) as is taught for treatment of angina pectoris.

SUMMARY OF THE INVENTION

Compositions and methods are provided for enhancing the retinal and/or choroidal blood flow for treatment of ocular conditions involving inadequate blood flows and nutrient supply. The compositions are characterized by having tetra-substituted pyrazine. The compositions may be administered topically, individually, or in combination, in a form absorbable by ocular and optic nerve tissues.

DETAILED DESCRIPTION OF THE FIGURES

DETAILED DESCRIPTION OF THE SPECIFIC EMBODIMENTS

Figure 1:
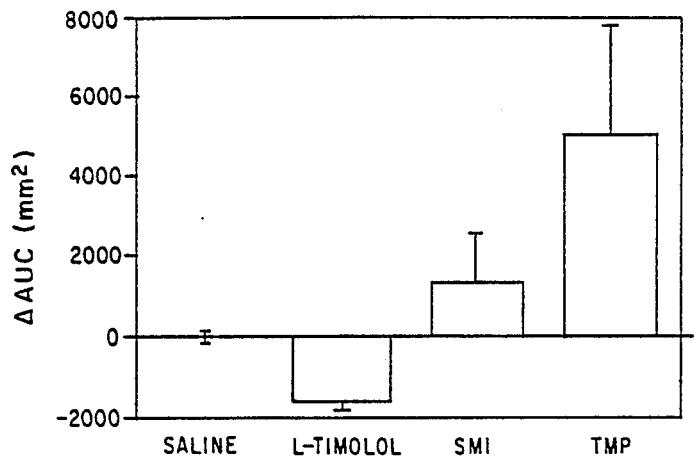
FIG. 1 is a chart illustrating the effects of tetramethylpyrazine hydrochloride (TMP), SMI (Tanshinones A1 and A2, *Saliva miltiorrhiza* injection) and L-timolol on rabbit retinal and choroidal blood flow measured with the laser Doppler method.

Methods and compositions are provided for treating ophthalmic conditions involving inadequate retinal and choroidal blood flow with ophthalmic formulations comprising as an active ingredient a tetra-substituted pyrazine, particularly a tetraalkyl-substituted pyrazine. The formulations will normally involve the active compound in a physiologically acceptable medium, which may be administered topically, parenterally, intravenously, or orally in a form available to retinal tissue. Compounds of particular interest are from naturally occurring medicinal plants and analogs thereof. For the most part, the compounds of this invention will be of the formula:

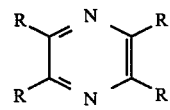

wherein:

each of the R's may be the same or different and will be alkyl of from 1 to 3 carbon atoms, preferably methyl.

The pyrazines may be present either as the base or its physiologically acceptable salts, particularly the hydrochloride.

The subject compounds are formulated to provide for treatment and/or prevention of retinal and optic nerve degeneration, including glaucoma, resulting from insufficient blood supply to retina, choroid, and optic nerve tissues. In some instances, the compound may also serve to increase coronary blood flow to benefit angina pectoris, an important consideration with middle-aged or older patients. The compounds are formulated in concentrated formulations in a form absorbable by ocular and optic nerve tissue.

The formulations can be conveniently comprised of one or more active agents and mixed with a physiologically acceptable carrier, particular liquid or ointment, where the carrier may be an organic or inorganic carrier. These carriers will vary depending upon the manner of application. Physiologically acceptable carriers include water, phosphate-buffered saline, saline, aqueous solvents, where water is mixed with lower alkanols, vegetable oils, polyalkylene glycols, petroleum-based jelly, ethyl cellulose, ethyl oleate, carboxymethyl cellulose, polyvinylpyrrolidine, isopropyl myristate and other conventional acceptable carriers and additives.

Additives may include substances which serve for emulsifying or preserving, wetting agents, bodying agents, and the like, which are employed conventionally in pharmaceutical preparations. Examples of such substances are polyethylene glycols 200–600, carbowaxes 1,000–10,000, antibacterial components such as quaternary ammonium compounds, phenylmercuric salts, e.g. thimerosal, methyl and propyl paraben, benzyl alcohol, phenethanol, etc. Other ingredients may include salts or buffering agents such as sodium chloride, sodium borate, sodium phosphate, sodium acetate, gluconate, and the like, where the pH will be maintained approximately neutral to mildly acidic, generally in the range of about 4.5 to 7.5.

Other additives which may find use include various compounds having wetting, chelating, or surfactant properties, either ionic or non-ionic, such as sorbitan monolaurate, triethanolamine oleate, polyoxyethylenesorbitan monopalmitate, dioctyl sodium sulfosuccinate, monothioglycerol, thiosorbitol, ethylenediaminetetraacetic acid, etc.

Desirably, the formulation will be isotonic and various salts or other additives may be employed to achieve an isotonic composition.

Besides liquids and ointments, solids may be employed which may be used as solid inserts. The solid insert will be in the form suitable for insertion into the cul-de-sac of the eye. The active ingredient may be included with a non-bioerodible insert, i.e., an insert which remains essentially intact during dispensing of the drug; or a bioerodible insert, i.e., one that dissolves or disintegrates, particularly by the effect of lacrimal fluids. Suitable inserts are described in U.S. Pat. No. 4,521,414, which disclosure is incorporated in by reference.

The dosage of the active ingredient will vary widely, depending upon the nature of the active ingredient and the manner in which the active ingredient is dispensed. Usually, for systemic administration, the active ingredient will be in the general range of 0.5–50 mg/kg of host weight, more usually from about 0.5–20 mg/kg of host weight. For topical administration, the concentration will generally range from about 0.01–5%, more usually from about 0.1–0.5% or equivalent weight ratio with a solid media.

The following examples are offered by way of illustration and not by way of limitation.

Experimental

EXAMPLE 1

Measurement of Retinal and Choroidal Blood Flow (RCBF) with Laser Doppler Method The laser Doppler method is based on the Doppler principle to monitor the perfusion of red blood cells in the microcirculatory bed of the retina and choroid (Goldman, *Current Laser Technology in Medicine and Surgery* (Springer, 1981) Ch. 5). Basically, the frequency of light back-scattered from moving red blood cells is shifted (Doppler shift) in proportion to the velocity of cells. A beam of concentrated light is focused onto the retina and choroid. The reflected light is guided through an optical fiber onto a photodetector. The flow calculation is dependent on the average velocity and the density of the cells in the measured volume. The resulting photocurrent, which contains the desired information on the speed of red blood cells is processed by means of a frequency-to-voltage converter. The output of the processing unit can be displayed both digitally and as a record tracing.

New Zealand white female rabbits weighing 3.0–3.5 kg were anesthetized with 30 mg/kg i.v. pentobarbital sodium followed 1 hr later with 0.5 g/kg i.v. urethane. Additional urethane was given throughout the experiment depending on the depth of anesthesia. With these anesthetics the eyes were immobilized sufficiently for measurement of retinal and choroidal blood flow using a laser Doppler (LD 5000 Capillary perfusion Monitor, Med Pacific Corporation, Seattle, WA). The femoral artery and vein were cannulated, respectively, for monitoring systemic blood pressure (RP-1500 Pressure Transducer and Model IVA Physiograph, Narco Biosystems, Houston, TX) and for injection of urethane and drugs. Heart rates were counted directly from the blood pressure pulse recordings. Drug solutions were adjusted to 1.5 ml for injection and were injected either slowly over a period of 60 sec or quickly as a pulse. Control experiments were done by injecting the same volume of saline. The experiment was run for at least 60 min after drug administration and readings of RCBF, systemic blood pressure and heart rate were taken at 10 min intervals.

Area under curve (AUC) was computed with a Hipad Digitizer (Houston Instrument) connected to an IBM Personal Computer XT.

It is clearly shown in FIG. 1 that TMP (10 mg/kg i.v.) increased retinal and choroidal blood flow markedly (52%) whereas L-timolol decreased it significantly ($-17\%$). Tanshinone (SMI) had a tendency to increase RBF (14%) but was not statistically significant.

EXAMPLE 2

Measurement of Blood Flow to Various Parts of the Eye with $^{85}$Sr-Microsphere Technique A radio-labeled microsphere technique (O'Day et al., *Arch. Ophthalmal.* (1971) 86: 205–209; Watanabe and Chiou, *Opthalmic Research* (1983) 15: 160–167) was used to determine blood flow to various eye tissues. New Zealand white rabbits weighing 2.5–3.5 kg were anesthetized with 30 mg/kg i.v. pentobarbital sodium. The left femoral artery was cannulated with PE 50 tubing; PE 90 tubing was inserted into the left ventricle through the right carotid artery. Heparin (1000 I.U.) was injected i.v. to prevent clotting. The blood flow was determined by injecting microspheres labeled with $^{85}$Sr (15.6$\pm$0.8 $\mu$sphere diameter, 3M Company, St. Paul, MN) into the left ventricle. The microspheres were suspended in 0.9% saline containing 1% Tween 80. The quantity of microspheres injected was approximately $1\times10^6$ (in 0.18–0.02 ml) per animal. The blood was collected from the femoral artery cannula for 60 sec at 10 sec after the injection of microspheres. The rabbit was then sacrificed with 5 ml i.v. saturated KCl solution. The eyes were removed quickly and the iris, ciliary body, retina, and choroid isolated. All tissues were weighed and their radioactivities determined with a Packard Auto-Gamma 500 (Packard Instruments Company, Downers Grove, IL). The blood flow in the tissues were calculated using the rate of blood flow through the femoral artery and its radioactivity as reference:

$$F = Q \times d'/d$$

where, F=blood flow of the tissue; Q=blood flow of femoral artery; d'=radioactivity counts/mg tissue; d=radioactivity counts in total blood collected from the femoral artery. The blood flow rate was expressed as $\mu l$/min/mg tissue. Forty microliter of TMP hydrochloride (2%) and SMI (tanshinones extracted from 1.5 g of *S. miltiorrhiza*/ml) were instilled to the eye 1.5 hours before sacrifice of the animal.

Data were analyzed with Student's t-test using an Apple IIe microcomputer. Values were considered significantly different from controls with $p > 0.05$.

As shown in Table 1, TMP increased blood flow to retina and choroid significantly. It also increased blood flow to iris and ciliary body. SMI increased blood flow significantly to all eye tissues except choroid. L-Timolol did not affect the blood flow to eye tissues significantly whereas moperone and trifluperidol suppressed it markedly.

TABLE 1

Effects of TMP and SMI on the Blood Flow of the Eye

| Treatment | N | Iris | Iris root-ciliary body | Retina | Chorid |
|---|---|---|---|---|---|
| Control | 7 | $106.8 \pm 10.5^a$ | $162.3 \pm 12.5$ | $7.3 \pm 1.4$ | $1308.0 \pm 227.7$ |
| TMP | 5 | $266.9 \pm 58.0^b$ | $382.3 \pm 65.7^b$ | $17.6 \pm 3.5^b$ | $2319.3 \pm 457.9^b$ |
| SMI | 5 | $217.1 \pm 57.5^b$ | $271.9 \pm 57.3^b$ | $13.3 \pm 2.7^b$ | $1931.5 \pm 656.2$ |

$a$, Value were expressed as mean $\pm$ SE $\mu l$/min/mg tissue.
$b$, $p < 0.05$ as compared to control.

EXAMPLE 3

Systemic Blood Pressure and Heart Rate

Female albino rabbits weighing 2.3–3.2 kg were anesthetized with 1 g/kg i.v. urethane. The left femoral artery was cannulated for measurement of blood pressure. The left femoral vein was cannulated for drug injection. Heart rates were taken from the blood pressure recording.

When TMP hydrochloride and SMI were administered intravenously over a period of 1 min, systemic blood pressure and heart rate were unaffected whereas L-Timolol significantly suppressed both of them as is shown in Table 2.

TABLE 2

Effects of TMP, SMI and L-Timolol on Blood Pressure Heart Rate and Retinal Blood Flow (RBF)

| Treatment | Blood Pressure (mmHg) | | Heart Rate (Beat/min) | | RBF |
|---|---|---|---|---|---|
| | Before | After | Before | After | % Changes |
| TMP | $103 \pm 12$ / $75 \pm 9$ | $101 \pm 10$ / $73 \pm 8$ | $290 \pm 18$ | $296 \pm 17$ | $+52\%^a$ |
| SMI | $86 \pm 10$ / $66 \pm 6$ | $87 \pm 9$ / $67 \pm 6$ | $286 \pm 29$ | $282 \pm 31$ | $+14\%$ |
| L-Timolol | $94 \pm 8$ / $76 \pm 7$ | $77 \pm 9^a$ / $61 \pm 6^a$ | $337 \pm 19$ | $143 \pm 20^a$ | $-17\%^a$ |

$a$Significantly different from controls at $p \leq 0.05$.

EXAMPLE 4

Lagendorff Heart Preparation

Guinea pigs of either sex weighing 240–350 g were stunned by a blow on the head. The heart with aortic arch was excised quickly and hung on the Lagendorff apparatus following the method of Trzeciakowski and Levi (Trzeciakowski and Levi, *J. Pharmacol Exp. Ther.* (1982) 223: 774–783). The heart was perfused with Ringer-Locke solution (NaCl, 154; KCl, 5.6; CaCl$_2$, 2.1; NaHCO$_3$, 6.0; glucose, 5.6 mM) maintained at 37° C. and oxygenated with 95% O$_2$/5% CO$_2$. The perfusion pressure was set at 38–40 mmHg. A polyethylene cannula was introduced into the left ventricular for monitoring left ventricle systolic pressure with a Statham P28 pressure transducer.

Figure 2:
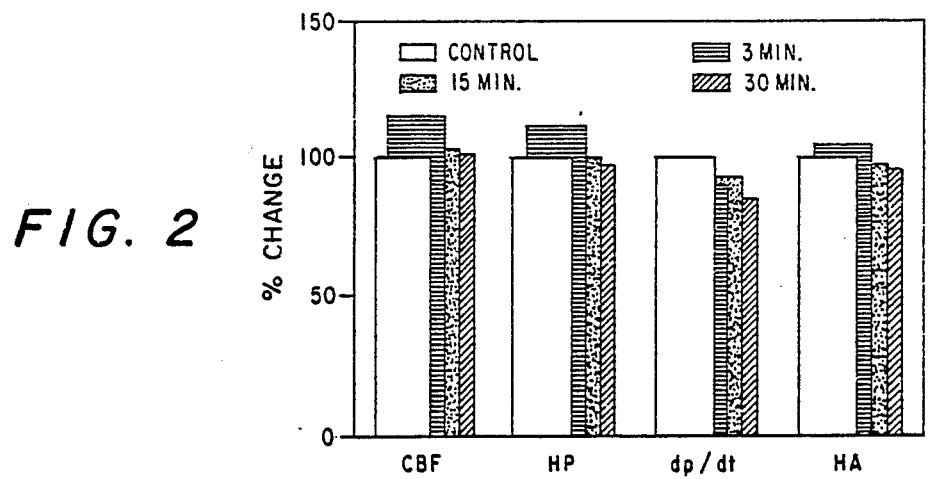
FIG. 2 is a chart illustrating the effects of TMP on isolated rabbit heart.

A pulse injection of TMP induced significant increase in coronary flow (FIG. 2) whereas intraventricular pressure, dp/dt, and heart rate were not significantly affected. These results indicate that TMP can be beneficial to patients who are suffering simultaneously with retinal degeneration and angina pectoris.

EXAMPLE 5

Isolated Vasculatures

Female albino rabbits weighing 2.2–3.0 kg were stunned and exsanguinated. The heart was removed and the ventral interventricular branches of the left epicardial coronary artery (with outside diameter of 0.5–0.8 mm) isolated. Renal, mesenteric and femoral arteries were then removed. The arteries were cut into ring segments and suspended individually in organ baths. Each vessel was bathed in 30 ml Kreb's solution (NaCl, 119; KCl, 4.7; NaHCO$_3$, 23; NaHPO$_4$, 1.2; CaCl$_2$, 1.8; MgCl$_2$, 1.2; and dextrose, 7.9 mM) oxygenated with 95% O$_2$/5% CO$_2$ and maintained at 37° C. The initial tension was adjusted to 1.0 g and each preparation was equilibrated in the organ bath for 60–80 min before initiation of experiments. During the equilibration period, Kreb's solution was replaced every 10–20 min. Muscle contractility was recorded with a Gould VC$_2$ force-displacement transducer on a Gould 2400 S recorder.

Figure 3:
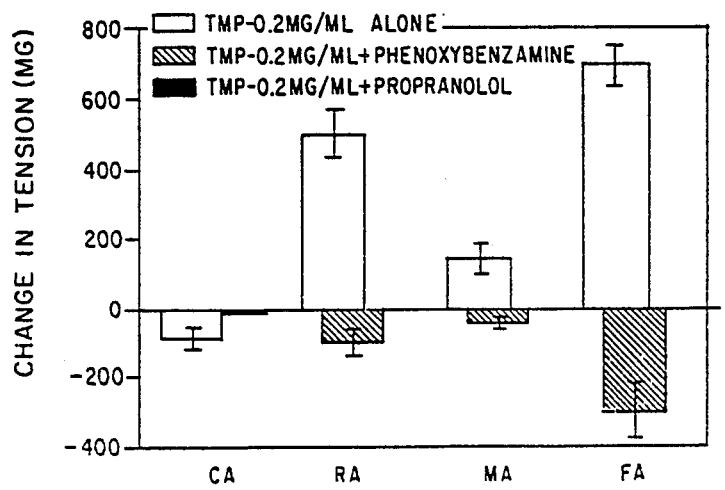
FIG. 3 is a chart illustrating the effects of TMP on various isolated blood vessels.

FIG. 3 shows clearly that TMP relaxed the coronary artery, but constricted renal, mesenteric and femoral arteries. The net result will be a relief of angina pectoris and maintenance of proper systemic blood pressure which are contrary to the side effects of L-timolol which causes cardiovascular suppression.

It is evident from the above results that the compounds of the subject invention provide for substantially enhanced retinal blood flow, while at the same time having no adverse effect on the systemic blood flow, with only moderate fluctuations, if any fluctuation at all. Thus, the compounds provide for unique results in not affecting the general cardiovascular system, while substantially enhancing retinal blood flow. The subject compounds may therefore be used in the treatment of a wide variety of ophthalmological diseases associated with reduced retinal blood flow and/or nutrient supply. The subject compounds can be administered to the host in a wide variety of ways, topically or systemically, so as to provide for the desired improvement in retinal and choroidal blood flow.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for enhancing ocular blood flow in a mammalian host suffering from an opthalmological disease associated with at least one of reduced retinal blood flow or reduced nutrient supply, said method comprising:

administering to said mammalian host an effective amount of a composition comprising: (1), in an amount sufficient to enhance at least one of retinal or chorodial blood flow, a tetrallkylpyrazine of from 8 to 16 carbon atoms or a physiologically acceptable salt thereof in a form absorbable by ocular and optic nerve tissues, and (2) an opthalmic carrier.

2. A method according to claim 1, wherein said tetraalkylpyrazine is tetramethylpyrazine.

3. A method according to claim 1, wherein said effective amount is in the range of 0.5-50 mg/kg of host.

4. A method according to claim 1, wherein said administering is with a solid ocular insert.

5. A method according to claim 1, wherein said administering is topical.

* * * * *

UNITED STATES PATENT AND TRADEMARK OFFICE
CERTIFICATE OF CORRECTION

PATENT NO. : 4,865,599

DATED : September 12, 1989

INVENTOR(S) : Chiou et al.

It is certified that error appears in the above-identified patent and that said Letters Patent is hereby corrected as shown below:

TITLE PAGE:

At [56], column 2, line 12, change "People' Liberation" to-- People's Liberation--.

At [73], change "Houston Biotechnology, Inc." to -- Houston Biotechnology Incorporated--.

At [75], change "Dominic M. Lam" to -- Dominic M-K. Lam--.

At [73], change "Woodlands, Tex." to -- The Woodlands, Texas--.

In column 1, line 50, change "interest o find" to-- interest to find--.

In column 1, line 63, change "septemic" to-- systemic--.

In column 8, line 15, change "chorodial" to -- choroidal--.

Signed and Sealed this

Twenty-third Day of April, 1991

Attest:

HARRY F. MANBECK, JR.

Attesting Officer

Commissioner of Patents and Trademarks